(12) United States Patent
Dayton et al.

(10) Patent No.: US 12,295,598 B2
(45) Date of Patent: May 13, 2025

(54) DEVICES AND METHODS FOR TREATING A STRICTURE ALONG THE BILIARY AND/OR PANCREATIC TRACT

(71) Applicants: BOSTON SCIENTIFIC SCIMED, INC., Maple Grove, MN (US); NORTHWESTERN UNIVERSITY, Evanston, IL (US)

(72) Inventors: Peter L. Dayton, Brookline, MA (US); Raymond D. Gessler, III, Roberts, WI (US); Srinadh Komanduri, Downers Grove, IL (US); Jason Matteson, Beldenville, WI (US); Mark P. Olson, New Brighton, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

(21) Appl. No.: 18/409,323

(22) Filed: Jan. 10, 2024

(65) Prior Publication Data
US 2024/0138860 A1 May 2, 2024

Related U.S. Application Data

(63) Continuation of application No. 17/393,814, filed on Aug. 4, 2021, now abandoned.
(Continued)

(51) Int. Cl.
*A61B 17/22* (2006.01)
(52) U.S. Cl.
CPC .... *A61B 17/22* (2013.01); *A61B 2017/22038* (2013.01); *A61B 2017/22042* (2013.01); *A61B 2017/22094* (2013.01)

(58) Field of Classification Search
CPC ............... A61B 17/22; A61B 17/3207; A61B 17/320758; A61B 17/320725;
(Continued)

(56) References Cited

U.S. PATENT DOCUMENTS

| | | | |
|---|---|---|---|
| 4,676,249 A | | 6/1987 | Arenas et al. |
| 4,794,928 A | * | 1/1989 | Kletschka ........ A61B 17/12136 606/159 |

(Continued)

FOREIGN PATENT DOCUMENTS

| | | |
|---|---|---|
| JP | 2008521503 A | 6/2008 |
| JP | 2010524631 A | 7/2010 |

(Continued)

OTHER PUBLICATIONS

International Search Report and Written Opinion for International Application No. PCT/US2021/044502, dated Dec. 7, 2021. (16 pages).

*Primary Examiner* — Tuan V Nguyen
(74) *Attorney, Agent, or Firm* — Seager, Tufte & Wickhem, LLP

(57) ABSTRACT

Medical devices and systems for treating a stricture, for example along the biliary and/or pancreatic tract, are disclosed. An example system may include a guidewire having a distal end and defining a lumen. A stiffening rod may be slidably disposed within the lumen. The stiffening rod may have a distal end and a distal end region disposed adjacent to the distal end. The stiffening rod may be configured to shift between a first position where the distal end of the stiffening rod is disposed proximally of the distal end of the guidewire and a second position where the distal end of the stiffening rod is disposed distally of the distal end of the guidewire.

17 Claims, 10 Drawing Sheets

Related U.S. Application Data

(60) Provisional application No. 63/061,509, filed on Aug. 5, 2020.

(58) Field of Classification Search
CPC .. A61B 17/320783; A61B 2017/22042; A61B 2017/22094; A61B 2017/22038; A61B 2017/32004; A61M 25/09041; A61M 25/09016; A61M 25/09025; A61M 2025/09091; A61M 2025/09116; A61M 2025/0915; A61M 2025/09175
See application file for complete search history.

(56) References Cited

U.S. PATENT DOCUMENTS

| | | |
|---|---|---|
| 5,527,298 A | 6/1996 | Vance et al. |
| 5,571,122 A * | 11/1996 | Kelly ............ A61B 17/320758 606/159 |
| 2006/0074442 A1 | 4/2006 | Noriega et al. |
| 2009/0198153 A1 | 8/2009 | Shriver |
| 2010/0049169 A1 | 2/2010 | Noriega et al. |
| 2010/0305475 A1 | 12/2010 | Hinchliffe et al. |
| 2012/0078232 A1 | 3/2012 | Schulting |
| 2014/0121642 A1 | 5/2014 | Jordan et al. |
| 2019/0321157 A1 | 10/2019 | Callaghan et al. |
| 2022/0054802 A1 | 2/2022 | Uchimura et al. |

FOREIGN PATENT DOCUMENTS

| | | |
|---|---|---|
| JP | 2014045848 A | 3/2014 |
| JP | 2016067374 A | 5/2016 |
| WO | 2006058223 A2 | 1/2006 |
| WO | 2008133808 A1 | 11/2008 |
| WO | 2009129394 A1 | 10/2009 |
| WO | 2020225935 A1 | 11/2020 |

* cited by examiner

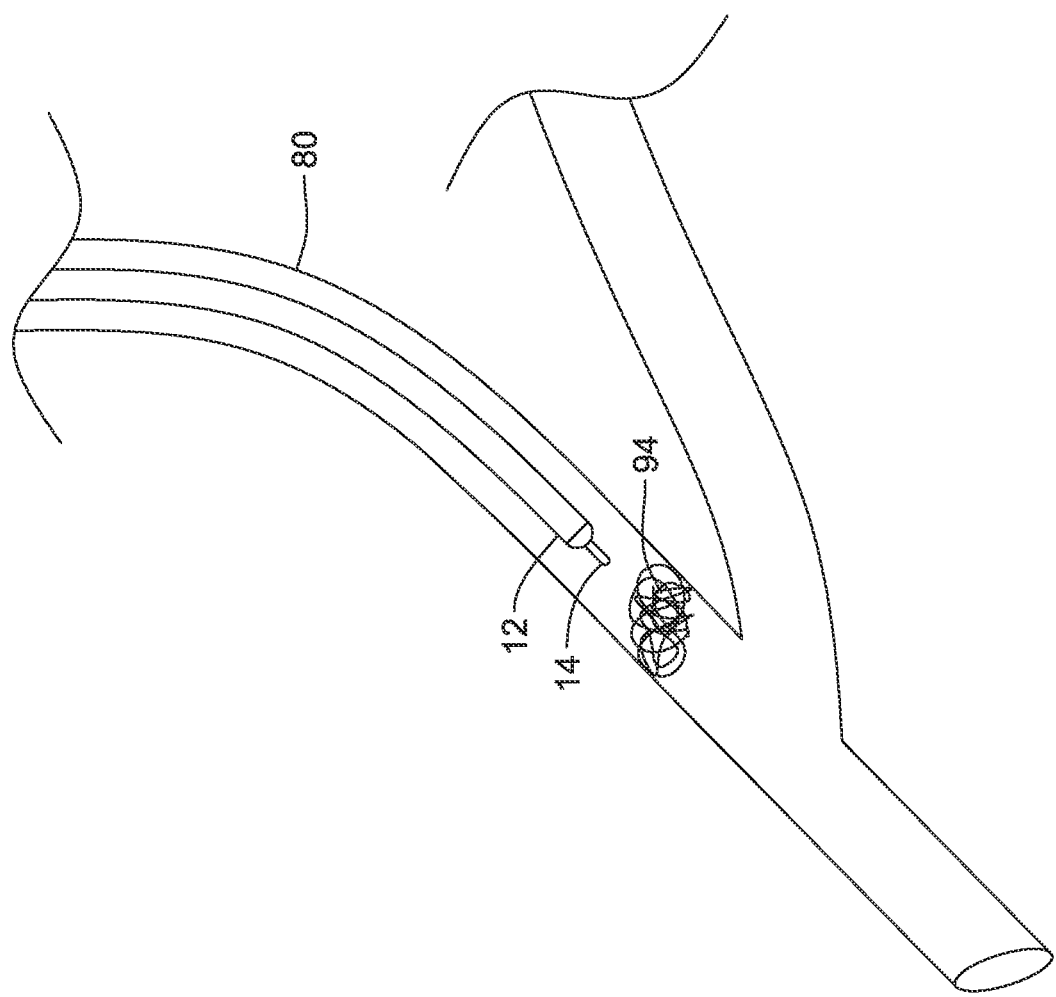

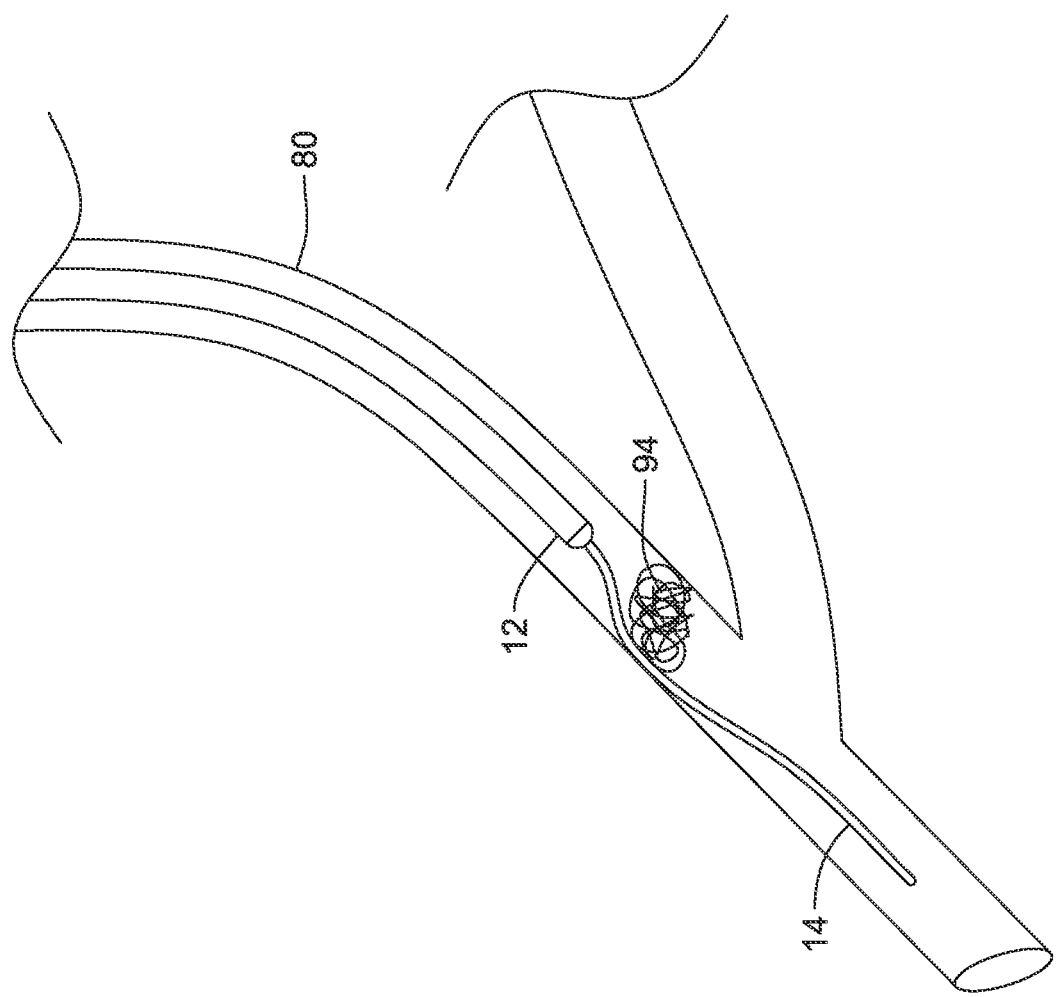

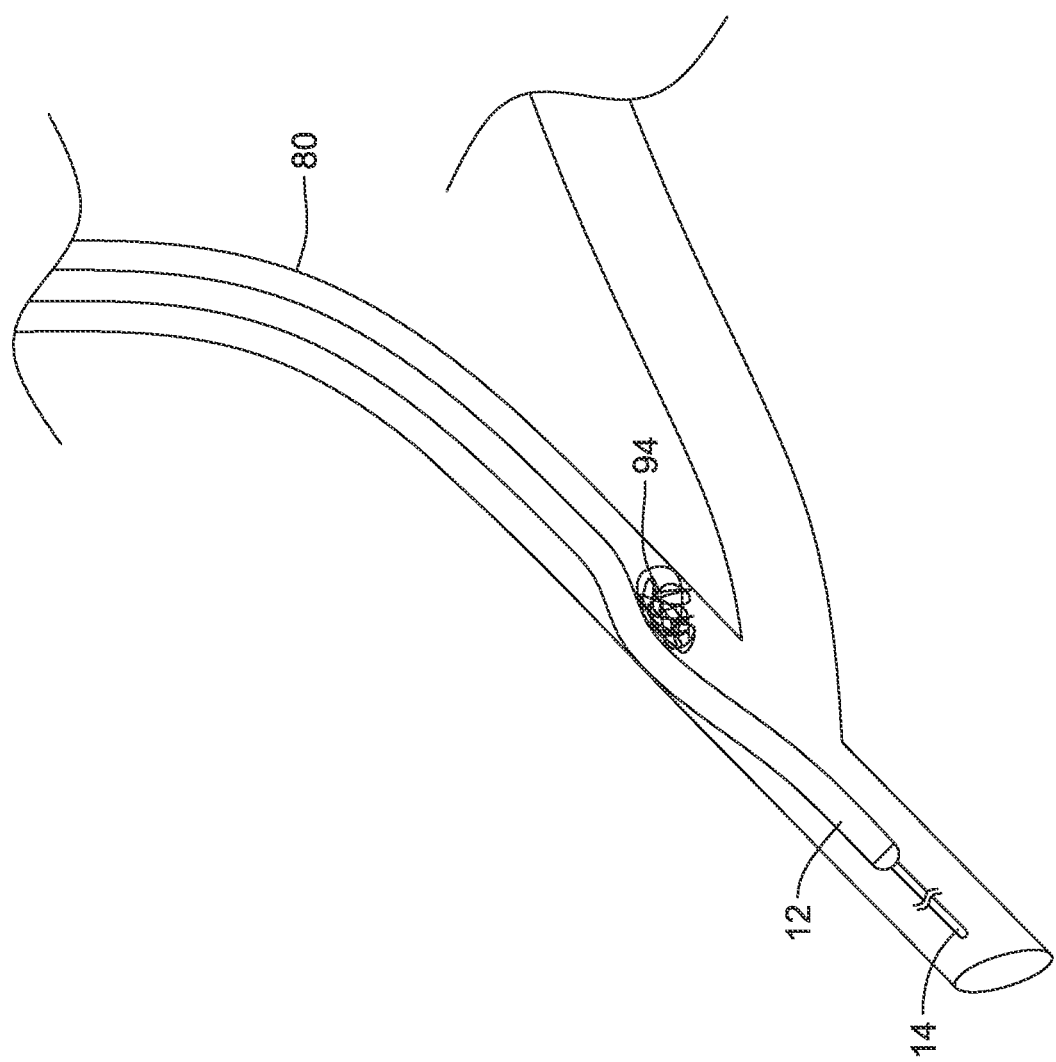

DEVICES AND METHODS FOR TREATING A STRICTURE ALONG THE BILIARY AND/OR PANCREATIC TRACT

CROSS REFERENCE TO RELATED APPLICATIONS

This application is a continuation of U.S. patent application Ser. No. 17/393,814, filed Aug. 4, 2021, which claims the benefit of and priority to U.S. Provisional Patent Application Ser. No. 63/061,509 filed on Aug. 5, 2020, the disclosures of which are incorporated herein by reference.

TECHNICAL FIELD

The present disclosure pertains to medical devices, and methods for manufacturing medical devices. More particularly, the present disclosure pertains to medical devices for treating strictures along the biliary and/or pancreatic tract.

BACKGROUND

A wide variety of medical devices have been developed for medical use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

SUMMARY

This disclosure provides design, material, manufacturing method, and use alternatives for medical devices. A system for treating a stricture is disclosed. The system comprises: a guidewire having a distal end and defining a lumen; a stiffening rod slidably disposed within the lumen, the stiffening rod having a distal end and a distal end region disposed adjacent to the distal end; and wherein the stiffening rod is configured to shift between a first position where the distal end of the stiffening rod is disposed proximally of the distal end of the guidewire and a second position where the distal end of the stiffening rod is disposed distally of the distal end of the guidewire.

Alternatively or additionally to any of the embodiments above, the guidewire comprises a tip region.

Alternatively or additionally to any of the embodiments above, the tip region includes a coil.

Alternatively or additionally to any of the embodiments above, the coil defines a passageway configured to accept the stiffening rod the passageway includes a tapered region.

Alternatively or additionally to any of the embodiments above, the tapered region defines a stop that limits distal translation of the stiffening rod through the passageway.

Alternatively or additionally to any of the embodiments above, the stiffening rod includes a shoulder region configured to engage the tapered region of the passageway.

Alternatively or additionally to any of the embodiments above, when the stiffening rod is at the first position, a proximal end of the distal end region is disposed adjacent to the distal end of the guidewire.

A method for crossing a stricture along the biliary and/or pancreatic tract is disclosed. The method comprises: advancing a guidewire system toward a stricture along the biliary and/or pancreatic tract, the guidewire system comprising: a guidewire having a distal end and defining a lumen, and a stiffening rod slidably disposed within the lumen, the stiffening rod having a distal end and a distal end region disposed adjacent to the distal end; shifting the stiffening rod from a first position where the distal end of the stiffening rod is disposed proximally of the distal end of the guidewire to a second position where the distal end of the stiffening rod is disposed distally of the distal end of the guidewire; and advancing the guidewire system beyond the stricture.

Alternatively or additionally to any of the embodiments above, the guidewire defines a passageway configured to accept the stiffening rod.

Alternatively or additionally to any of the embodiments above, the passageway defines a stop that limits distal translation of the stiffening rod through the passageway.

Alternatively or additionally to any of the embodiments above, advancing the guidewire system beyond the stricture includes advancing at least a portion of the stiffening rod beyond the stricture.

Alternatively or additionally to any of the embodiments above, further comprising advancing a medical device toward the stricture in a retrograde direction.

Alternatively or additionally to any of the embodiments above, further comprising engaging the portion of the stiffening rod beyond the stricture with the medical device.

Alternatively or additionally to any of the embodiments above, further comprising retracting the medical device, wherein retracting the medical device includes advancing the stiffening rod in an antegrade direction.

Alternatively or additionally to any of the embodiments above, wherein advancing the stiffening rod in an antegrade direction advances the guidewire beyond the stricture.

A system for treating a stricture is disclosed. The system comprises: a guidewire having an open distal end and defining a lumen; a stiffening rod slidably disposed within the lumen, the stiffening rod having a distal end and a distal end region disposed adjacent to the distal end; and wherein the stiffening rod is configured to shift between a first position where the distal end of the stiffening rod is disposed adjacent to the distal end of the guidewire and a second position where the distal end of the stiffening rod extends through the open distal end and is disposed distally of the distal end of the guidewire.

Alternatively or additionally to any of the embodiments above, the stiffening rod is configured to shift to a third position where the distal end of the stiffening rod is disposed distally of the distal end of the guidewire and where a proximal end of the distal end region is disposed adjacent to the distal end of the guidewire.

Alternatively or additionally to any of the embodiments above, the lumen includes a tapered region that defines a stop that limits distal translation of the stiffening rod.

Alternatively or additionally to any of the embodiments above, the stiffening rod includes a shoulder region configured to engaged the tapered region.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which:

FIGS. 6-10 illustrate an example method for using a medical device system according to the present disclosure.

Figure 1:
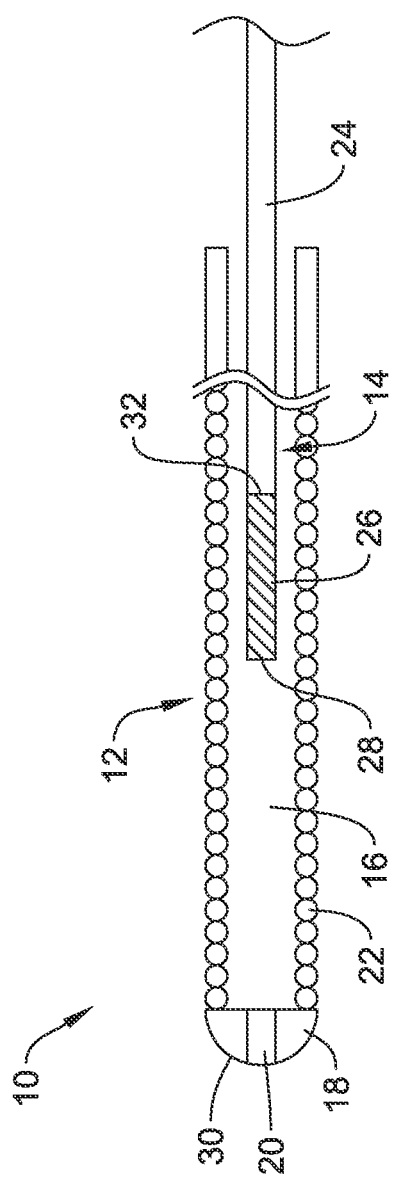
FIG. 1 is a partial cross-sectional side view of a portion of a medical device system according to the present disclosure.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

In endoscopy, a frequent medical condition arises when a patient presents with abdominal pain with or without associated jaundice. The etiology is usually some type of obstruction in the biliary tree which prevents bile from flowing naturally from the proximal tree into the duodenum. The blockage may be the result of biliary stones caught in the lumen of the ducts or a tumor which is either in the wall of the duct or impinging upon the wall from adjacent tissue. When such a stricture occurs the duct proximal to the stricture dilates and the duct distal to the stricture receives a reduced flow of bile. In order to relieve the patient's symptoms, gastroenterologists seek to find a method for resuming the flow of bile from the proximal dilated duct into the duodenum. Some interventions contemplated for relieving symptoms may include placing a stent across the stricture to drain the proximal duct, removing a stone, and/or the like.

The most common method of placing a stent across the stricture is to perform an endoscopic retrograde cholangio-pancreatography (ERCP) where a side-viewing endoscope is placed in the duodenum at the location of the biliary papilla and a guidewire is placed through the papilla and up the biliary duct, across the stricture, in a retrograde fashion. Such procedures may be challenging. For example, depending on the location, geometry, and mechanics of the stricture, deep cannulation of the proximal duct may be difficult if not be possible. Furthermore, when the physician attempts to access the biliary duct, they may inadvertently cannulate the pancreatic duct. Inadvertent cannulation of the pancreatic duct could lead to complications such as pancreatitis. Disclosed herein are devices and methods that address these and other issues, for example by utilizing antegrade (e.g., non-papillary) stricture crossing.

FIG. 1 schematically depicts an example medical device system 10. The system 10 may include a guidewire 12 and a stiffening rod 14 slidably disposed within a lumen 16 formed in the guidewire 12. In general, the stiffening rod 14 is configured to provide additional support (e.g., stiffening support) to the guidewire 12. The additional support may allow the guidewire 12, which may be generally flexible, to more easily pass a stricture such as a stricture along the biliary and/or pancreatic tract. The system 10 is generally designed to cross a structural along the biliary and/or pancreatic tract in an antegrade manner.

The structure and form of the guidewire 12 may vary. For example, the guidewire 12 may include a polymer tip, spring tip, and/or other configuration. In some instances, such as those where the guidewire 12 includes a spring or coil tip, the guidewire 12 may include a coil 22, which may define a part of the tip or tip region. In some instances, the coil 22 may have a proximal end that is disposed distally of the proximal end of the guidewire 12. In other instances, the coil 22 may extend substantially the full length of the guidewire 12. The coil 22 may also define a portion of the lumen 16, which may act as a passageway through which the stiffening rod 14 may pass through. The guidewire 12 may also include a distal tip 18 with an opening 20 formed therein. The opening 20 may allow the stiffening rod 14 to be passed therethrough such that a portion of the stiffening rod 14 can be advanced out distally from the guidewire 12.

The form of the stiffening rod 14 may vary. In some instances, the stiffening rod 14 may take the form of a metallic rod form from a suitable material such as stainless steel and/or other materials such as those disclosed herein. In some of these and in other instances, the stiffening rod 14 may include a proximal end region 24 and a distal end region 26. The distal end region 26 may include a generally atraumatic tip and may have a stiffness that is less than the proximal end region 24. For example, the distal end region 26 may include a relatively flexible material. In some instances, the distal end region 26 may include a shaft with a plurality of slits formed therein that increase the flexibility thereof relative to the proximal end region 24. Alternatively, may have a stiffness that is greater than the proximal end region 24. For example, the distal end region 26 may include a relatively stiff material that can be secured to the proximal end region 24. In other instances, the proximal end region 24 may include a shaft with a plurality of slits formed therein that increase the flexibility thereof relative to the distal end region 26 (e.g., which may be free of such slits).

Figure 2:
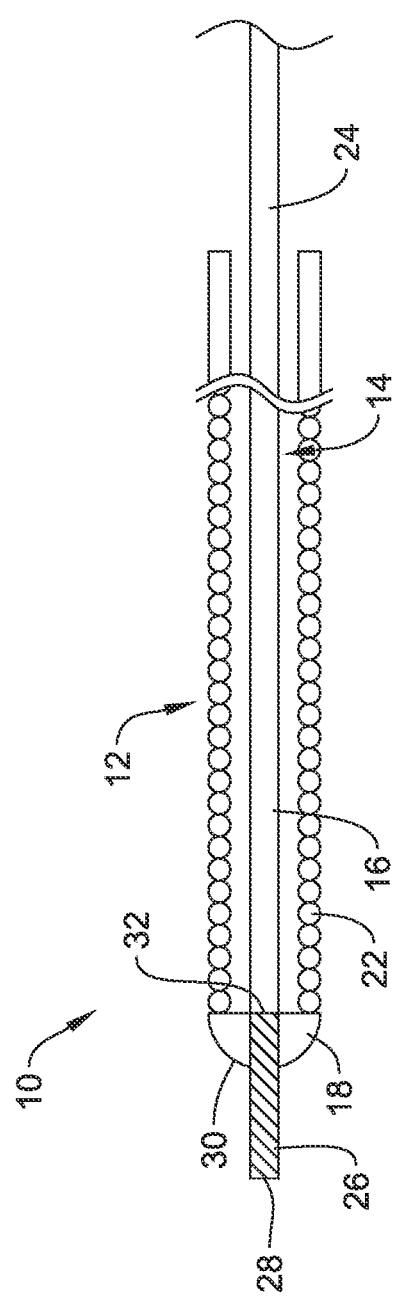
FIG. 2 is a partial cross-sectional side view of a portion of a medical device system according to the present disclosure.
Figure 3:
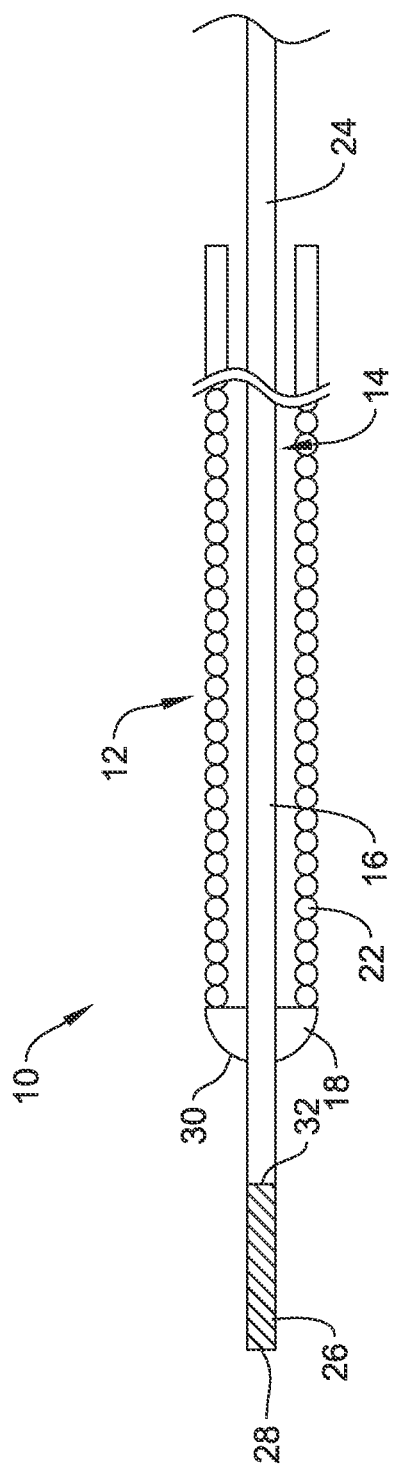
FIG. 3 is a partial cross-sectional side view of a portion of a medical device system according to the present disclosure.

As indicated herein, the stiffening rod 14 may be configured to slide within the lumen 16 of the guidewire 12 between a number of different positions. For example, in FIG. 1, a distal end 28 of the stiffening rod 14 is disposed proximally of a distal end 30 of the guidewire 12. FIG. 2 illustrates the stiffening rod 14 in another position where the distal end 28 is disposed distally of the distal end of the guidewire 12. In this example, a proximal end 32 of the distal end region 26 is disposed adjacent to the distal end 30 of the guidewire 12. FIG. 3 illustrates the stiffening rod 14 in another position where the distal end 28 is disposed distally of the distal end of the guidewire 12. In this example, the proximal end 32 of the distal end region 26 is also disposed distally of the distal end 30 of the guidewire 12.

Figure 4:
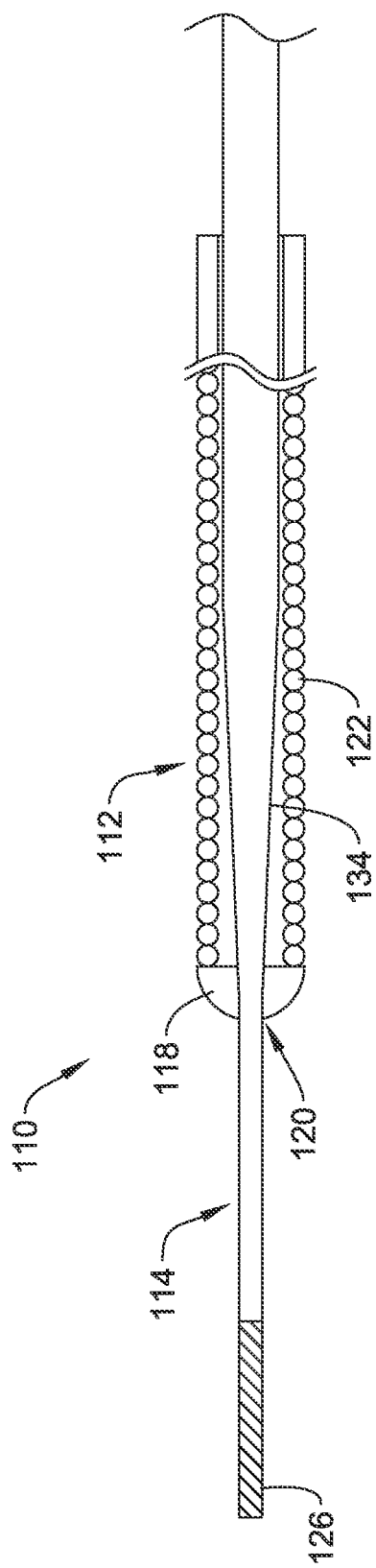
FIG. 4 is a partial cross-sectional side view of a portion of a medical device system according to the present disclosure.

FIG. 4 illustrates another example system 110 that may be similar in form and function to other systems disclosed herein. The system 110 may include a guidewire 112 and a stiffening rod 114. The stiffening rod 114 may include a distal end region 126. In this example, the stiffening rod 114 may include a tapered region or shoulder 134. The shoulder 134 may transition the diameter of the stiffening rod 114 to a diameter that is larger than the opening 120 in the tip 118 (and/or that is larger than the passageway formed within the coil 122). As such, the shoulder 134 may engage the opening 120 (and/or the coil 122) in a manner that limits further distal translation of the stiffening rod 114 through the guidewire 112.

Figure 5:
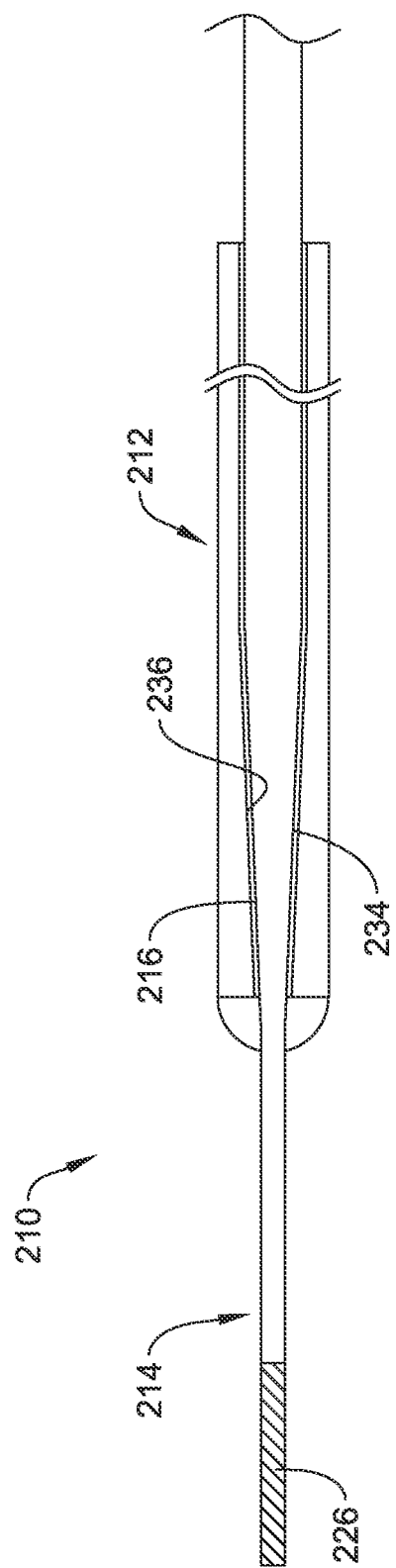
FIG. 5 is a partial cross-sectional side view of a portion of a medical device system according to the present disclosure.

FIG. 5 illustrates another example system 210 that may be similar in form and function to other systems disclosed herein. The system 210 may include a guidewire 212 and a stiffening rod 214. The stiffening rod 214 may include a distal end region 226. The stiffening rod 214 may include a tapered region or shoulder 234. The guidewire 212 may include a stop 236 along the lumen 216. In this example, the stop 236 takes the form of a tapered region along the guidewire 212. The shoulder 234 may engage the stop 236 in a manner that limits further distal translation of the stiffening rod 114 through the guidewire 112.

Figure 6:
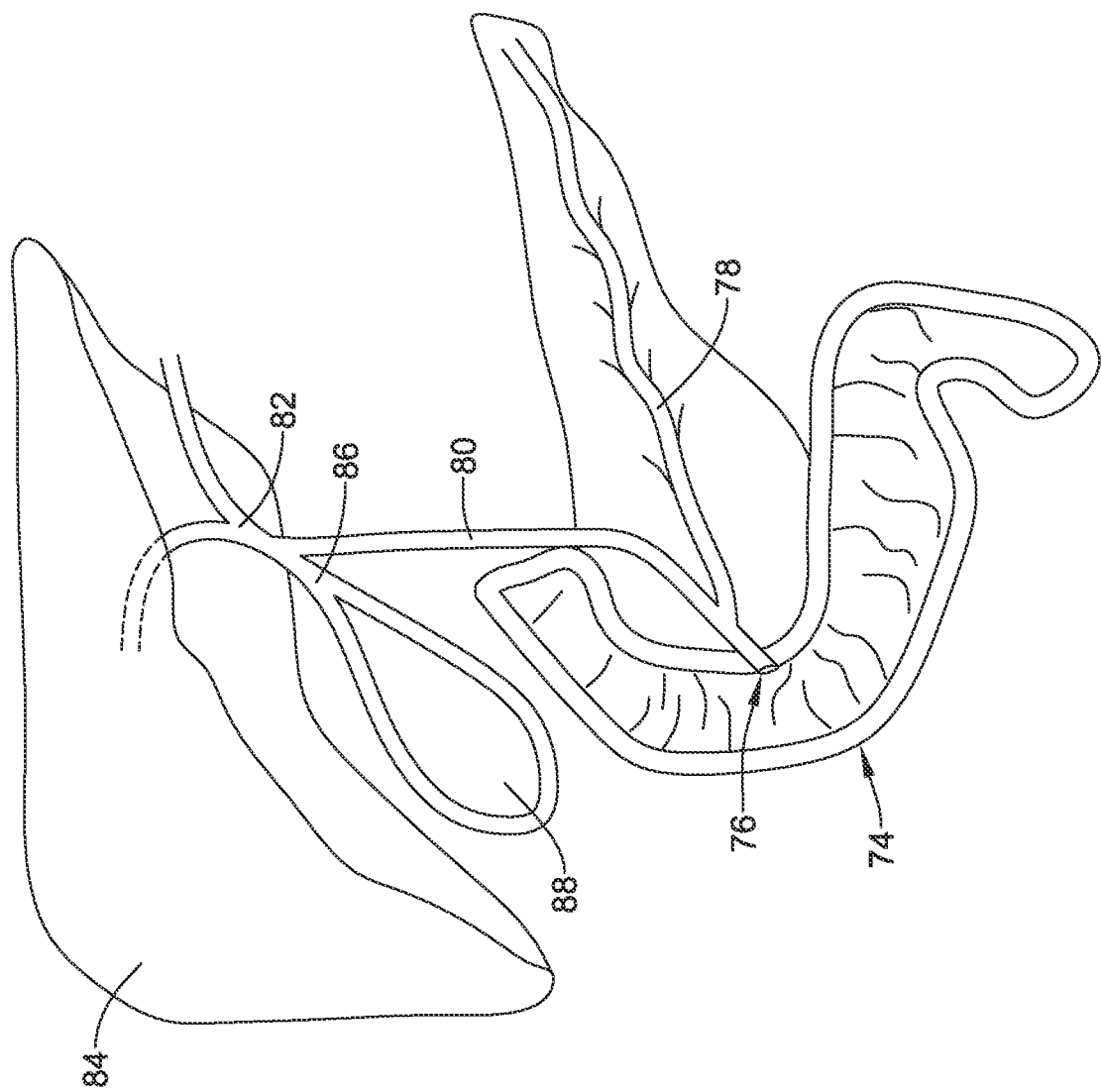

FIG. 6 illustrates an overview of the biliary system or tree. A portion of the duodenum 74 is shown. The papilla of Vater 76 (e.g., also known as the ampulla of Vater or simply the papilla) is located at the illustrated portion of the duodenum 74. The papilla 76 generally forms the opening where the pancreatic duct 78 and the common bile duct 80 can empty into the duodenum 74. The hepatic ducts, denoted by the reference numeral 82, are connected to the liver 84 and empty into the bile duct 80. Similarly, the cystic duct 86, being connected to the gall bladder 88, also empties into the bile duct 80. In general, an endoscopic or biliary procedure may include advancing a medical device to a suitable location along the biliary tree and then performing the appropriate intervention.

Figure 7:
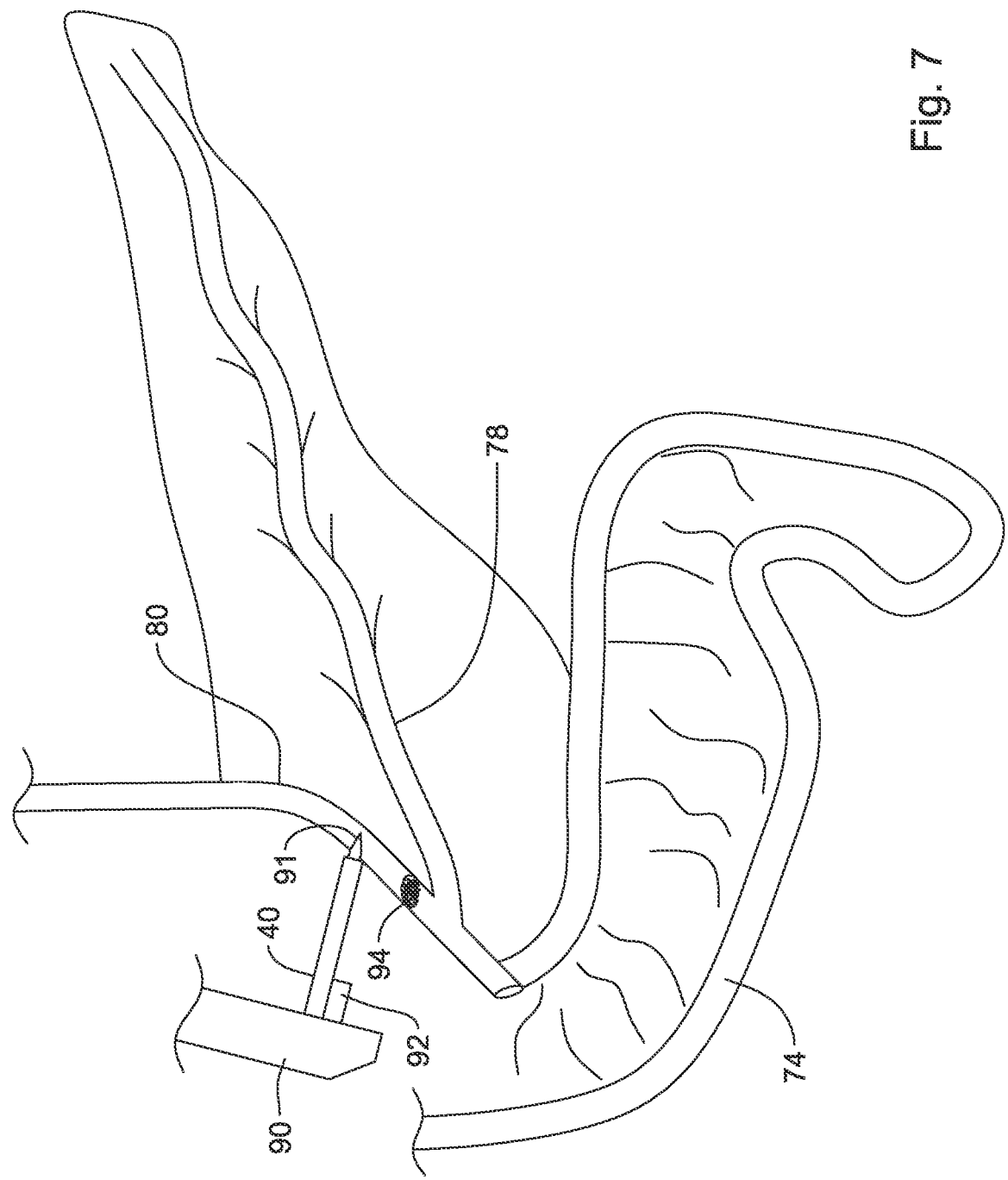

In some instances, it may be desirable to navigate the guidewire 12 and/or the stiffening rod 14 past a stricture 94 along the pancreatic and/or biliary tract. For example, FIG. 7 depicts an endoscope 90 extending into the duodenum 74. In some instances, a catheter or introducer sheath 40 may be advanced through the endoscope 90 (e.g., through a channel formed in the endoscope 90). The introducer sheath 40 may be directed toward the wall of the duodenum 74 with the elevator 92 of the endoscope 90. In some instances, a needle/sharp 91 may be disposed within the introducer sheath 40. The needle/sharp 91 may help to pierce through the wall of the duodenum 74, through tissue, and into a position along the pancreatic and/or biliary tract adjacent to a stricture 94. In this example, the stricture 94 is disposed along the bile duct 80.

In order to cross the stricture 94, the guidewire 12 may be navigated toward the stricture 94 as depicted in FIG. 8. When doing so, the stiffening rod 14 may be disposed in a position/configuration where a portion of the stiffening rod 14 extends distally beyond the distal end of guidewire 12. In some instances, the stiffening rod 14 may be further advanced beyond the stricture as depicted in FIG. 9. In instances where the guidewire 12 and/or stiffening rod 14 include a stop/shoulder/taper, such as the case with guidewire 112, 212 and/or stiffening rod 114, 214, another medical device may be able to approach the stiffening rod 14 from the retrograde (duodenal/papillary) side and engage the stiffening rod 14. The additional medical device may be used to pull on the stiffening rod 14. When doing so, the shoulder/taper (e.g., the shoulder 134, 234) on the stiffening rod 14 (e.g., the stiffening rod 114, 214) may engage the tip 118, coil 122, and/or stop 236 on the guidewire 12 (e.g., the guidewire 112, 212) to limit further translation of the stiffening rod 14 through the guidewire 12. As the additional medical device is further pulled, the engagement between the shoulder/taper (e.g., the shoulder 134, 234) on the stiffening rod 14 (e.g., the stiffening rod 114, 214) with the tip 118, coil 122, and/or stop 236 on the guidewire 12 (e.g., the guidewire 112, 212) may allow the guidewire 12 to be pulled beyond/across the stricture 94 as depicted in FIG. 10. This may include pulling the stiffening rod 14, guidewire 12, or both through the papilla 76 and into the duodenum 74. With the stiffening rod 14, guidewire 12, or both in the duodenum 74, another treatment device such as a stone grabber, stent delivery system, or the like could be advanced in a retrograde manner over the guidewire 12 toward/across the stricture 94.

The materials that can be used for the various components of the devices disclosed herein may include those commonly associated with medical devices. For simplicity purposes, the following discussion makes reference to the guidewire 12. However, this is not intended to limit the devices and methods described herein, as the discussion may be applied to other similar tubular members and/or components of tubular members or devices disclosed herein.

The guidewire 12 and/or the stiffening rod 14 may be made from or otherwise includes a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), high-density polyethylene, low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:
1. A method for navigating around a stricture along a biliary and/or pancreatic tract, the method comprising:
   advancing a guidewire system toward a stricture along the biliary and/or pancreatic tract, the guidewire system comprising:
      a guidewire having a distal end and defining a lumen, and
      a stiffening rod slidably disposed within the lumen, the stiffening rod having a distal end and a distal end region disposed adjacent to the distal end;
   shifting the stiffening rod from a first position where the distal end of the stiffening rod is disposed proximally of the distal end of the guidewire to a second position where the distal end of the stiffening rod is disposed distally of the distal end of the guidewire; and
   advancing the guidewire system beyond the stricture by navigating around the stricture without penetrating through the stricture.
2. The method of claim 1, wherein the guidewire defines a passageway configured to accept the stiffening rod.
3. The method of claim 2, wherein the passageway defines a stop that limits distal translation of the stiffening rod through the passageway.
4. The method of claim 3, wherein advancing the guidewire system beyond the stricture includes advancing at least a portion of the stiffening rod beyond the stricture.
5. The method of claim 4, further comprising advancing a medical device toward the stricture in a retrograde direction.
6. The method of claim 5, further comprising engaging the portion of the stiffening rod beyond the stricture with the medical device.
7. The method of claim 6, further comprising retracting the medical device, wherein retracting the medical device includes advancing the stiffening rod in an antegrade direction.
8. The method of claim 7, wherein advancing the stiffening rod in an antegrade direction advances the guidewire beyond the stricture.
9. A method for navigating around a stricture along a biliary and/or pancreatic tract, the method comprising:
   advancing a guidewire system toward a stricture along the biliary and/or pancreatic tract, the guidewire system comprising:
      a guidewire having a distal end and defining a lumen, and
      a stiffening rod slidably disposed within the lumen, the stiffening rod having a distal end and a distal end region disposed adjacent to the distal end;
   advancing the distal end region of the stiffening rod distally of the distal end of the guidewire such that the distal end of the stiffening rod extends distally beyond the stricture by navigating around the stricture without penetrating through the stricture;
   thereafter, advancing the guidewire along the stiffening rod distally beyond the stricture.
10. The method of claim 9, further comprising:
   advancing a medical device toward the stricture in a retrograde direction.
11. The method of claim 10, further comprising:
   engaging the distal end region of the stiffening rod beyond the stricture with the medical device.
12. The method of claim 11, further comprising:
   pulling the stiffening rod in an antegrade direction with the medical device.
13. The method of claim 9, wherein the guidewire includes a stop that limits distal translation of the stiffening rod through the lumen of the guidewire.
14. The method of claim 13, wherein the stop includes a tapered surface.
15. A method for crossing a stricture along a biliary and/or pancreatic tract, the method comprising:
   advancing a guidewire system toward a stricture along the biliary and/or pancreatic tract, the guidewire system comprising:
      a guidewire having a distal end and defining a lumen, and a stiffening rod slidably disposed within the lumen, the stiffening rod having a distal end and a distal end region disposed adjacent to the distal end;

advancing the distal end region of the stiffening rod distally of the distal end of the guidewire such that the distal end of the stiffening rod extends distally beyond the stricture while the distal end of the guidewire is proximal of the stricture;

advancing a medical device toward the stricture in a retrograde direction; and engaging the distal end region of the stiffening rod beyond the stricture with the medical device.

16. The method of claim 15, further comprising:

pulling the stiffening rod in an antegrade direction with the medical device.

17. The method of claim 15, wherein the guidewire includes a stop that limits distal translation of the stiffening rod through the lumen of the guidewire.

* * * * *